US00PP33043P3

(12) United States Plant Patent
Koekkoek

(10) Patent No.: US PP33,043 P3
(45) Date of Patent: May 11, 2021

(54) CARNATION PLANT NAMED 'HILTASHA'

(50) Latin Name: ***Dianthus caryophyllus* L.**
Varietal Denomination: Hiltasha

(71) Applicant: HilverdaFlorist B.V., De Kwakel (NL)

(72) Inventor: Arthur N. J. Koekkoek, Alkmaar (NL)

(73) Assignee: Hilverder Roust B.V., De Kwakel (NL)

( * ) Notice: Subject to any disclaimer, the term of this patent is extended or adjusted under 35 U.S.C. 154(b) by 0 days.

(21) Appl. No.: 16/873,728

(22) Filed: Jun. 16, 2020

(65) Prior Publication Data

US 2020/0396881 P1 Dec. 17, 2020

Related U.S. Application Data

(60) Provisional application No. 62/921,431, filed on Jun. 17, 2019.

(51) Int. Cl.
*A01H 5/02* (2018.01)
*A01H 6/30* (2018.01)

(52) U.S. Cl.
USPC ..... Plt./272
CPC ..... *A01H 6/305* (2018.05)

(58) Field of Classification Search
USPC ..... Plt./272
See application file for complete search history.

*Primary Examiner* — Susan McCormick Ewoldt
(74) *Attorney, Agent, or Firm* — C. Anne Whealy

(57) ABSTRACT

A new and distinct cultivar of Carnation plant named 'Hiltasha', characterized by its compact, upright to broadly spreading and uniformly mounding plant habit; freely branching habit; early and freely flowering habit; purple-colored single flowers; and good container and garden performance.

1 Drawing Sheet

Botanical designation: *Dianthus caryophyllus* L.
Cultivar denomination: 'HILTASHA'.

CROSS-REFERENCED TO CLOSELY-RELATED APPLICATIONS

Title: Varieties of Carnation Plants
Inventor/Applicant: Arthur Koekkoek
Filed: Jun. 17, 2019
Ser. No. 62/921,431
Inventor & Applicant hereby claim the benefit of this provisional U.S. Plant Patent.

STATEMENT REGARDING PRIOR DISCLOSURES BY INVENTOR & APPLICANT

An European Community Plant Breeder's Rights application for the instant plant was filed by the Applicant, HilverdaFlorist B. V. of De Kwakel, The Netherlands on Aug. 20, 2019, application number 2019/2011. Foreign priority is not claimed to this application.

The Inventor & Applicant assert that no publications nor advertisements relating to sales, offers for sale or public distribution occurred more than one year prior to the effective filing date of this application. Any information about the claimed plant would have been obtained from a direct or indirect disclosure from the Inventor or the Applicant. Inventor & Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of Carnation plant, botanically known as *Dianthus caryophyllus* L., grown commercially as a container plant and hereinafter referred to by the name 'Hiltasha'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in May, 2013 of a proprietary selection of *Dianthus caryophyllus* L. identified as code number 2242, not patented, as the female, or seed, parent with a proprietary selection of *Dianthus caryophyllus* L. identified as code number D 1152, not patented, as the male, or pollen, parent. The new Carnation plant was discovered and selected by the Inventor as a single flowering plant from within the progeny of the stated cross-pollination in a controlled greenhouse environment in De Kwakel, The Netherlands in June, 2014.

Asexual reproduction of the new Carnation plant by terminal cuttings propagated in a controlled greenhouse environment in De Kwakel, The Netherlands since March, 2015 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hiltasha'.

These characteristics in combination distinguish 'Hiltasha' as a new and distinct Carnation plant:

1. Compact, upright to broadly spreading and uniformly mounding plant habit.
2. Freely branching habit.
3. Early and freely flowering habit.
4. Purple-colored single flowers.
5. Good container and garden performance.

Plants of the new Carnation differ primarily from plants of the female parent selection in the following characteristics:

1. Leaves of plants of the new Carnation are broader and are darker green in color than leaves of plants of the female parent selection.
2. Plants of the new Carnation are more freely-flowering than plants of the female parent selection.

Plants of the new Carnation differ primarily from plants of the male parent selection in the following characteristics:

1. Plants of the new Carnation have green-colored leaves whereas plants of the male parent selection have greyed green-colored leaves.
2. Plants of the new Carnation are more freely-branching than plants of the male parent selection.
3. Plants of the new Carnation flower earlier than plants of the male parent selection.

Plants of the new Carnation also can be compared to plants of *Dianthus superbus* 'Holkahori', not patented. In side-by-side comparisons, plants of the new Carnation differ primarily from plants of 'Holkahori' in the following characteristics:

1. Leaves of plants of the new Carnation are broader than leaves of plants of 'Holkahori'.
2. Flowers of plants of the new Carnation are flatter than and not as cupped as flowers of plants of 'Holkahori'.
3. Flowers of plants of the new Carnation are purple in color whereas flowers of plants of 'Holkahori' are red purple in color.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph (FIG. 1) comprises a side perspective view of a typical flowering plant of 'Hikasha' grown in a container.

DETAILED BOTANICAL DESCRIPTION

Plants used in the aforementioned photograph and following observations and measurements were grown during the late winter and early spring in 10.5-cm containers in a glass-covered greenhouse in De Kwakel, The Netherlands and under cultural practices typical of commercial container Carnation production. During the production of the plants, day temperatures ranged from 16° C. to 20° C. and night temperatures ranged from 16° C. to 18° C. Plants used for the photograph and description were three months from planting and were pinched one time about one week after planting rooted young plants. In the following description, color references are made to The Royal Horticultural Society Colour Chart, 2015 Edition, except where general terms of ordinary dictionary significance are used.

Botanical classification: *Dianthus caryophyllus* L. 'Hikasha'.

Parentage:

*Female, or seed, parent.*—Proprietary selection of *Dianthus caryophyllus* L. identified as code number 2242, not patented.

*Male, or pollen, parent.*—Proprietary selection of *Dianthus caryophyllus* L. identified as code number D 1152, not patented.

Propagation:

*Type.*—By terminal vegetative cuttings.

*Time to initiate roots, summer.*—About six days at temperatures ranging from 20° C. to 25° C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; white in color, actual color of the roots is dependent on substrate composition, water quality, fertilizer type and formulation, substrate temperature and physiological age of roots.

*Rooting habit.*—Moderate branching; medium density.

Plant description:

*Plant and growth habit.*—Herbaceous perennial, typically grown as a container plant; compact, uniformly mounding, upright to broadly spreading plant habit; moderately vigorous growth habit; slow to moderate growth rate.

*Plant height, soil level to top of foliar plane.*—About 15.9 cm.

*Plant height, soil level to top of floral plane.*—About 16.7 cm.

*Plant diameter or spread.*—About 27.4 cm.

*Lateral branches.*—Branching habit: Freely branching habit with about 20 main (basal) stems; each main stem with about six lateral branches; pinching is not required, however, pinching will enhance lateral branch development. Length: About 9.3 cm. Diameter: About 2 mm. Internode length: About 2.9 cm. Strength: Strong. Aspect: About 45° from vertical. Texture and luster: Smooth, glabrous; moderately glossy. Color, developing: Close to 145B. Color, developed: Close to 137B; proximally, close to 145B.

Leaf description:

*Arrangement.*—Opposite, simple; sessile.

*Length.*—About 5.5 cm.

*Width.*—About 6.5 mm.

*Shape.*—Narrowly oblanceolate to close to linear; slightly carinate.

*Apex.*—Acute.

*Base.*—Attenuate; decurrent.

*Margin.*—Entire; not lobed.

*Texture and luster, upper and lower surfaces.*—Smooth, glabrous; matte.

*Venation pattern.*—Parallel; only midvein is discernible.

*Color.*—Developing leaves, upper surface: Close to 143A to 143B; proximally, close to 144C. Developing leaves, lower surface: Close to 143A to 143B; proximally, close to 144A to 144B. Fully expanded leaves, upper surface: Close to NN137A; venation, close to NN137B. Fully expanded leaves, lower surface: Close to 137B; venation, close to 144B.

Flower description:

*Flower form and flowering habit*.—Rotate single-type flowers arranged singly or in pairs; freely flowering habit with about 70 flower buds and flowers per plant at one time; flowers face mostly upright to slightly outwardly.

*Natural flowering season*.—Flowering is continuous from the spring to late summer in The Netherlands; plants begin flowering about 13 weeks after planting.

*Postproduction longevity*.—Flowers last about ten days on the plant; flowers not persistent.

*Fragrance*.—Faintly fragrant; clove-like, sweet and pleasant.

*Flower buds*.—Length: About 2.2 cm. Diameter: About 5 mm. Shape: Narrowly oblong. Texture and luster: Smooth, glabrous; matte. Color: Close to 146A to 146B strongly tinged with close to between N186C and 200A; developing petal apices, close to 72C.

*Flower diameter*.—About 3.3 cm.

*Flower depth*.—About 2.8 cm.

*Petals*.—Quantity and arrangement: About five petals arranged in a single whorl. Length: About 3.5 cm. Width: About 1.6 cm. Shape: Free part, spatulate. Apex: Praemorse. Base: Narrowly cuneate. Margin: Distally, dentate; proximally, entire; moderately undulate. Texture and luster, upper and lower surfaces: Smooth, glabrous; velvety; matte. Color: When opening, upper surface: More intense than NN78A; towards the base, close to 145B. When opening, lower surface: More intense than NN78C; towards the base, close to 145B. Fully opened, upper surface: Close to NN78A, marbled with close to NN78B and NN78C; towards the base, close to 145B; venation, similar to lamina colors; colors do not change with development. Fully opened, lower surface: Close to NN74B; towards the base, close to 145B; venation, similar to lamina colors; colors do not change with development.

*Sepals*.—Quantity and arrangement: Five sepals arranged in a single whorl; proximal 70% portion of the sepals are fused into a campanulate-shaped calyx. Calyx length: About 2 cm. Calyx diameter: About 5.5 mm. Sepal length: About 1.9 cm. Sepal width, at base of "free" portion: About 3.5 mm. Shape: Narrowly oblong. Apex: Acute. Margin: Entire. Texture and luster, upper surface: Smooth, glabrous; glossy. Texture and luster, lower surface: Smooth, glabrous; matte. Color: When opening, upper surface: Close to 146D; towards the base, close to 145B; apical margins tinged with close to 186A. When opening, lower surface: Close to 146A to 146B strongly tinged with close to between N186C and 200A; apical margins, close to 185D. Fully opened, upper surface: Close to 146D; towards the base, close to 145B; apical margins tinged with close to 186A. Fully opened, lower surface: Close to 147C; towards the base, close to 144C; distally, strongly tinged with close to between N186C and 200A; apical margins, close to 185D.

*Peduncles*.—Length: About 4.4 cm. Diameter: About 1.5 mm. Strength: Strong. Aspect: About 12.5° from the stem axis. Texture and luster: Smooth, glabrous; moderately glossy. Color: Close to 137A.

*Pedicels* (*flowers in pairs*).—Length: About 1.6 cm. Diameter: About 1.25 mm. Strength: Moderately strong. Aspect: About 10° from the peduncle axis. Texture and luster: Smooth, glabrous; moderately glossy. Color: Close to 137C.

*Reproductive organs*.—Stamens: Quantity: Typically ten. Filament length: About 2.1 cm. Filament color: Close to 155D. Anther size: About 2 mm by 0.75 mm. Anther shape: Irregularly oblong, dorsifixed. Anther color: Close to 186C. Pollen: Moderate. Pollen color: Close to 156C to 156D. Pistils: Quantity: About two per flower. Pistil length: About 2.3 cm. Stigma diameter: About 0.5 mm. Stigma shape: Pointed, spirally curved, feathery in appearance. Stigma color: Close to NN155D. Style length: About 1.3 cm. Style color: Close to NN155D. Ovary color: Close to between 145A and 150B. Fruits and seeds: To date, fruit and seed development have not been observed on plants of the new Carnation.

Pathogen & pest resistance: To date, plants of the new Carnation have not been observed to be resistant to pathogens and pests common to Carnation plants.

Garden performance: Plants of the new Carnation have been observed to tolerate rain, wind, high temperatures about 35° C. and to be suitable for USDA Hardiness Zones 5 to 9.

It is claimed:

1. A new and distinct Carnation plant named 'Hiltasha' as illustrated and described.

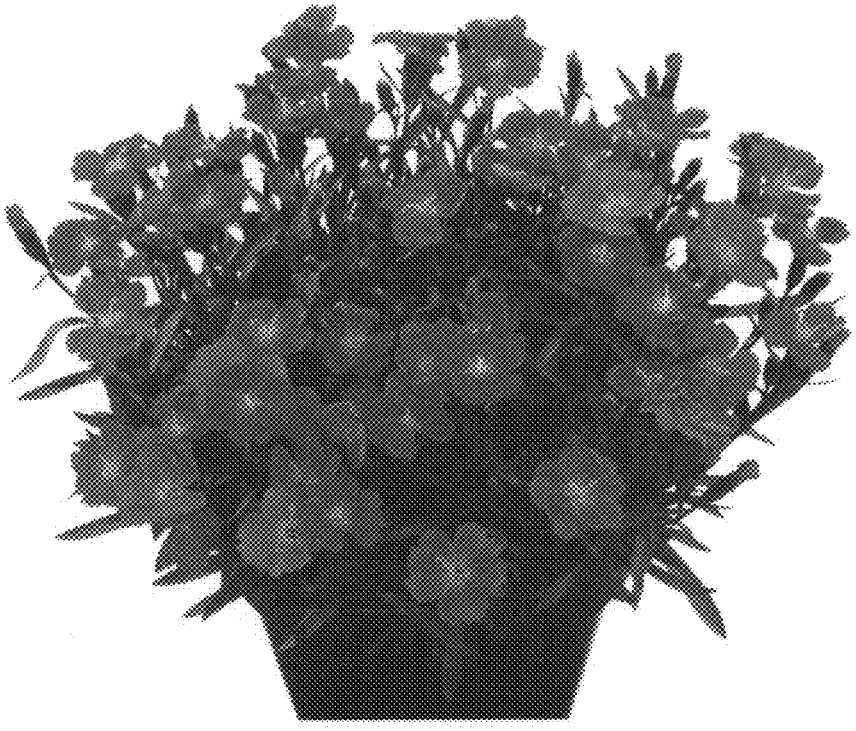

* * * * *